(12) United States Patent
Benn et al.

(10) Patent No.: US 9,295,632 B1
(45) Date of Patent: Mar. 29, 2016

(54) COMPOSITIONS COMPRISING LATEX POLYMERS AND METHODS FOR ALTERING THE COLOR OF HAIR

(71) Applicant: L'OREAL, Paris (FR)

(72) Inventors: Mark Benn, Union, NJ (US); Michael Degeorge, Old Bridge, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/573,609

(22) Filed: Dec. 17, 2014

(51) Int. Cl.
*A61Q 5/00* (2006.01)
*A61Q 5/10* (2006.01)
*A61K 8/81* (2006.01)
*A61K 8/41* (2006.01)

(52) U.S. Cl.
CPC .............. *A61K 8/8147* (2013.01); *A61K 8/41* (2013.01); *A61K 8/8152* (2013.01); *A61Q 5/10* (2013.01); *A61K 2800/43* (2013.01); *A61K 2800/4324* (2013.01)

(58) Field of Classification Search
CPC ..... A61K 8/41; A61K 8/8152; A61K 8/8147; A61K 2800/43; A61K 2800/4324
USPC ...................................................... 424/70.16
See application file for complete search history.

(56) References Cited

U.S. PATENT DOCUMENTS

| 3,110,695 | A | 11/1963 | Ceresa |
| 3,304,273 | A | 2/1967 | Stamberger |
| 3,383,351 | A | 5/1968 | Stamberger |
| 3,412,054 | A | 11/1968 | Milligan et al. |
| 3,523,095 | A | 8/1970 | Laurito et al. |
| 4,798,721 | A | 1/1989 | Yahagi et al. |
| 5,441,728 | A | 8/1995 | Tsaur et al. |
| 6,126,929 | A | 10/2000 | Mougin |
| 2002/0010970 | A1* | 1/2002 | Cottard et al. ............... 8/405 |
| 2005/0089490 | A1 | 4/2005 | Jachowicz et al. |
| 2011/0150802 | A1* | 6/2011 | Bui et al. ................. 424/63 |

FOREIGN PATENT DOCUMENTS

| DE | 1152536 B | 8/1963 |
| GB | 1040452 A | 8/1966 |

* cited by examiner

*Primary Examiner* — Eisa Elhilo
(74) *Attorney, Agent, or Firm* — The Marbury Law Group, PLLC

(57) ABSTRACT

Disclosed are compositions for controlling or slowing down the coloration of keratin fibers such as hair wherein the compositions comprise at least one film-forming latex polymer, at least one neutralizing agent, and at least one organic solvent, and water, wherein the pH of the composition is from about 2 to about 6. Methods for controlling or slowing down the coloration of hair using the compositions are also disclosed.

25 Claims, No Drawings

COMPOSITIONS COMPRISING LATEX POLYMERS AND METHODS FOR ALTERING THE COLOR OF HAIR

TECHNICAL FIELD

The present disclosure relates to compositions for controlling the coloration process on keratin substrates, for instance human keratin fibers such as the hair, comprising providing a composition comprising at least one film-forming latex polymer, at least one neutralizing agent, at least one organic solvent, and water.

BACKGROUND OF THE INVENTION

It is known that consumers desire to use cosmetic and personal care compositions that enhance the appearance of keratin fibers such as hair by changing the color of the hair and/or by imparting various properties to hair such as shine and conditioning. The process of changing the color of hair can involve either depositing an artificial color onto the hair which provides a different shade or color to the hair or lifting the color of the hair, such as for example, from a dark brown shade to a medium brown or a light brown shade.

However, there are difficulties presented with obtaining consistent and uniform color on hair when consumers dye or alter the color of their hair. For example, the hair will grow out, creating a visible demarcation line between the regrowth of the roots and the last dye session. Artificial color on hair also has the tendency to fade over time, especially during the shampooing process, resulting in a dull or matte look to the hair fiber. Furthermore, the processing times for hair color compositions vary greatly for undyed virgin hair (not chemically processed hair) and heavily colored or chemically processed hair. The level of skill required to preserve the condition of overly colored and processed hair when applying a fresh coat of hair color while also maintaining a uniform shade of color from root to tip is very high.

It has now been discovered that by providing an acidic hair pretreatment composition comprising at least one film-forming latex polymer, a neutralizing agent, an organic solvent and water, it is possible to form a film or coating on a substrate that has certain desirable properties, such as a protective barrier that will control or slow down the coloration process. Said compositions may be used prior to dyeing to either enhance or reduce the dye penetration into the fiber. Said compositions may also be applied on overly chemically processed hair before coloring or altering the color of the hair in order to preserve the condition of the hair and to also provide a uniform color of the hair from the root to the tip. In particular, the compositions can be used in re-coloring or re-dyeing the hair. Typically, a visible demarcation line at a point along the shaft of artificially colored hair can be observed as new hair grows out from the roots As the hair grows out, the color of the hair from the demarcation line down the length of the hair is generally different from the color of the new hair. Accordingly, the hair pretreatment compositions of the invention, that aid in the uniform distribution of coloring agents onto the hair fiber or in obtaining uniformly colored hair along the length of the hair fiber or in satisfactory gray hair coverage can be useful in increasing the efficiency of hair coloring agents and/or of hair coloring processes.

In addition, applying the acidic pretreatment composition of the present invention onto hair in order to create a barrier or coating on hair may also be useful in highlighting, lowlighting, and bleaching of hair. Such a barrier or coating allows the selective coloration or alteration of the color of portions of hair while leaving other portions of hair unchanged and/or uncolored, resulting in color alterations only in selected portions of the hair. Accordingly, the acidic hair pretreatment compositions of the invention can also aid in achieving a multi-toned or multi-colored or highlighted or lowlighted hair in a more convenient and easy manner.

Surprisingly and unexpectedly, the inventors have discovered that using an acidic pretreatment composition on hair before coloring or altering the color of the hair wherein the composition comprises a film-forming latex polymer, a neutralizing agent, an organic solvent and water resulted in a method for controlling or slowing down the coloration of the hair in order to allow for more uniform hair coloring. The current invention allows for easy and improved coloration of the hair fibers to get a uniform hair color from root to ends of the hair. When applied starting from the visible demarcation line which is generally in the middle of the hair shaft (midshaft) down the length of artificially colored hair, the pretreatment composition of the invention will create a barrier or coating on the hair to impede a subsequent hair color altering or hair coloring composition from penetrating into the shaft as fast as it would without the pretreatment composition on the hair.

BRIEF SUMMARY OF THE INVENTION

The present invention relates to an acidic hair pretreatment composition for controlling or slowing down the coloration of hair, the composition comprising:
  a) From about 2.5% to about 10% by weight, based on a dry weight basis, of at least one film-forming latex polymer;
  b) at least one neutralizing agent;
  c) from about 1% to about 20% by weight, of at least one organic solvent; and
  d) water;
wherein the pH of the composition is from about 2 to about 6; all weights being relative to the total weight of the composition.

The present invention also relates to methods for controlling or slowing down the coloration of hair involving applying onto hair, the above-described acidic pretreatment composition, followed by the application of a hair color altering composition.

DETAILED DESCRIPTION OF THE INVENTION

It has been unexpectedly and surprisingly discovered that the compositions and methods of the present invention provide hair color benefits onto keratin fibers such as hair which allow for more uniform hair coloring.

Without being bound by theory, it is believed that combinations of a film-forming latex polymer, a neutralizing agent, an organic solvent, and water in an acidic system provide compositions that impart films or coatings on the surface of keratin fibers such as hair which inhibit, reduce or enhance color deposit, thereby creating equal or uniform deposit of hair color from the roots to the ends of the hair shaft.

The composition of the present invention is particularly useful as a hair pretreatment composition.

As used herein, the expression "at least one" means one or more and thus includes individual components as well as mixtures/combinations.

It is also to be understood that, as used herein the terms "the," "a," or "an," mean "at least one," are understood to encompass the plural as well as the singular and should not be limited to "only one" unless explicitly indicated to the contrary. Thus, for example, the use of "an acid" is intended to mean at least one acid.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The term "comprising" (and its grammatical variations) as used herein is used in the inclusive sense of "having" or "including" and not in the exclusive sense of "consisting only of".

"Keratin fiber" as used herein, includes, but is not limited to hair, such as hair on the human head and eyelashes.

"Film former" or "film-forming latex polymer" as used herein means a polymer or resin that leaves a film on the substrate to which it is applied, for example, after a solvent accompanying the film former has evaporated, absorbed into and/or dissipated on the substrate. These terms may also refer to a polymer capable, by itself or in the presence of an auxiliary film forming polymer, of forming a continuous or a discontinuous film that adheres to a support and especially to keratin substrates such as keratin fibers or hair.

"Film former" or "film-forming latex polymer" as used herein may also be referred to as fixing polymers when such polymers are employed to fix or keep keratin fibers in a particular configuration or shape or arrangement.

Among the film-forming latex polymers that may be used in the hair pretreatment composition as disclosed herein, non-limiting mention may be made of cationic latex polymers, anionic latex polymers, nonionic latex polymers, amphoteric latex polymers, or mixtures thereof.

"Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

As used herein, the terms "applying a composition onto keratin fibers" and "applying a composition onto hair" and variations of these phrases are intended to mean contacting the fibers or hair, with at least one of the compositions of the invention, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present invention onto keratin fibers such as hair.

The terms "controlling" or "slowing down" (and its grammatical variations) as used herein include inhibiting hair color from penetrating into a keratin fiber such as hair; or inhibiting dye molecules or color-altering agents including but not limited to oxidative dyes, direct dyes, couplers, oxidation dye precursors, inorganic pigments, organic pigments, bleaching agents, lightening agents, lifting agents, or oxidizing agents from developing in their maximum capacity; or impeding dye molecules or color-altering agents from developing at a normal processing time by creating a film or coating barrier on a keratin fiber such as hair.

The terms "controlling" or "slowing down" (and its grammatical variations) as used herein also can refer to the reduction of the amount of color altering agent(s) that is deposited on or penetrate the hair fiber by creating a film barrier on a keratin fiber such as hair.

As used herein, the terms "method of controlling the coloration of hair," "method of slowing down the coloration of hair" or "method for controlling the variation in the artificial color of hair" is understood to mean any method for modifying the appearance of the keratin fibers or the hair with respect to their melanin or pigment or their artificial color. When the keratin fibers comprise hair on the human head, the term "method of controlling the coloration of hair," "method of slowing down the coloration of hair" or "method for controlling the variation in the artificial color of hair" is also understood to mean any method for coloring or dyeing or pigmenting or otherwise altering the shade of the hair.

The compositions and methods of the present invention can comprise, consist of, or consist essentially of the essential elements and limitations of the invention described herein, as well as any additional or optional ingredients, components, or limitations described herein or otherwise useful.

Unless otherwise specified herein, all percentages and ratios of components are by weight relative to the total weight of the final composition.

In an embodiment, the present invention relates to an acidic hair pretreatment composition, comprising:
  a) from about 2.5% to about 10% by weight, based on a dry weight basis, of at least one film-forming latex polymer;
  b) at least one neutralizing agent;
  c) from about 1% to about 20% of at least one organic solvent; and
  d) water;
wherein the pH of the composition is from about 2 to about 6; all weights being relative to the total weight of the composition.

In an embodiment, the present invention relates to a method of coloring hair, said method comprising:
(1) applying onto hair, an acidic pretreatment hair composition comprising:
  a) from about 2.5% to about 10% by weight, based on a dry weight basis, of at least one film-forming latex polymer;
  b) at least one neutralizing agent;
  c) from about 1% to about 20% by weight, at least one organic solvent; and
  d) water;
wherein the pH of the composition is from about 2 to about 6; all weights being relative to the total weight of the composition; and
(2) applying onto the hair, a hair color altering composition.

In an embodiment, the present invention relates to a method of coloring hair, said method comprising:
(1) applying onto hair, an acidic pretreatment hair composition comprising:
  a) from about 2.5% to about 10% by weight, based on a dry weight basis, of at least one film-forming latex polymer selected from Acrylates copolymer (Aculyn 33 or Luviflex® Soft or Daitosol 5000AD), Acrylates/Hydroxyesters Acrylates Copolymer (Acudyne 180), Polyacrylate-2 Crosspolymer (Fixate Superhold™), Styrene/Acrylic copolymer (Neocryl® A-1120), Acrylates/Ethylhexyl Acrylate Copolymer (Daitosol 5000SJ), Polyurethane-34 (BAYCUSAN® C1000), Polyurethane-34 (BAYCUSAN® C1001), Polyurethane-32 (BAYCUSAN® C1003), Polyurethane-35 (BAYCUSAN® C1004), Polyurethane-48 (BAYCUSAN® C1008), Polyurethane-1 (Luviset® P.U.R), Polycarbamyl Polyglycon Ester (Neorez® R989) and mixtures thereof.
  b) at least one neutralizing agent;
  c) from about 3% to about 8% by weight, at least one organic solvent; and
  d) water;
wherein the pH of the composition is from about 2 to about 6; all weights being relative to the total weight of the composition; and
(2) applying onto the hair, a hair color altering composition.

In an embodiment, the present invention relates to an acidic pretreatment hair composition for controlling or slowing down the coloration of hair, the composition comprising:
  a) from about 2.5% to about 8% by weight, based on a dry weight basis, of acrylates copolymer, acrylates/hydroxyesters acrylates copolymer and mixtures thereof;
  b) from about 0.01% to about 2% by weight of at least one neutralizing agent;
  c) from about 1.5% to about 8% by weight of at least one organic solvent selected from ethylene glycol monopropyl ether, ethylene glycol monobutyl ether, propylene glycol monomethyl ether, propylene glycol monopropyl ether, propylene glycol monobutyl ether, diethylene glycol monoethyl ether, diethylene glycol monobutyl ether, dipropylene glycol n-butyl ether, and mixtures thereof; and
  d) water;
wherein the pH of the composition is from about 2 to about 6; all weights being relative to the total weight of the composition.

In one embodiment, the present invention relates to a method for controlling or slowing down the coloration of hair, the method comprising:
(1) applying onto hair, an acidic pretreatment hair composition, comprising:
  a) from about 2.75% to about 8% by weight, based on a dry weight basis, of acrylates copolymer, acrylates/hydroxyesters acrylates copolymer and mixtures thereof;
  b) from about 0.1% to about 1% by weight of at least one neutralizing agent;
  c) from about 3% to about 8% by weight of at least one organic solvent selected from ethylene glycol monopropyl ether, ethylene glycol monobutyl ether, propylene glycol monomethyl ether, propylene glycol monopropyl ether, propylene glycol monobutyl ether, diethylene glycol monoethyl ether, diethylene glycol monobutyl ether, dipropylene glycol n-butyl ether, and mixtures thereof; and
  d) water;
wherein the pH of the composition is from about 2 to about 6; all weights being relative to the total weight of the composition; and
(2) applying onto the hair, a hair color altering composition.

In one embodiment, the present invention relates to a method for controlling the variation in the artificial color of hair, the method comprising:
(1) applying onto the mid-shaft up to the ends of the hair, an acidic pretreatment hair composition, comprising:
  a) from about 3% to about 5.5% by weight, based on a dry weight basis, of acrylates copolymer, acrylates/hydroxyesters acrylates copolymer and mixtures thereof;
  b) from about 0.01% to about 5% by weight of at least one neutralizing agent;
  c) from about 0.5% to about 30% by weight of at least one organic solvent; and
  d) water;
wherein the pH of the composition is from about 2 to about 6; all weights being relative to the total weight of the composition; and
(2) applying onto the roots up to the ends of the hair, a hair color altering composition.

In another embodiment, the present invention relates to a kit comprising:
(1) an individually packaged hair pretreatment composition comprising:
  a) from about 2.5 to about 10% by weight, based on a dry weight basis, of at least one film-forming latex polymer;
  b) at least one neutralizing agent;
  c) from about 3% to about 5% by weight, of at least one organic solvent; and
  d) water;
  wherein the pH of the composition is from about 2 to about 6; all weights being relative to the total weight of the composition;
(2) an individually packaged composition comprising a color-altering agent selected from oxidative dye precursors, direct dyes, pigments, lightening agents, bleaching agents, oxidizing agents, and mixtures thereof; and
(3) optionally, an individually packaged composition comprising at least one oxidizing agent.

In one embodiment, the present invention relates to a system for controlling the coloration of hair, the system comprising:
(1) an acidic hair pretreatment composition comprising:
  a) from about 2.5 to about 8% by weight, based on a dry weight basis, of at least one film-forming latex polymer;
  b) at least one neutralizing agent;
  c) from about 1.5% to about 8% by weight, of at least one organic solvent; and
  d) water;
wherein the pH of the composition is from about 2 to about 6; all weights being relative to the total weight of the composition;
(2) a composition comprising a color-altering agent selected from oxidative dye precursors, direct dyes, pigments, lightening agents, bleaching agents, oxidizing agents, and mixtures thereof; and
(3) optionally, a composition comprising at least one oxidizing agent.

In another embodiment, the present invention relates to a method of making an acidic pretreatment composition for application on the hair comprising:
(1) combining
  a) from about 3% to about 5.5% by weight, based on a dry weight basis, of at least one film-forming latex polymer.
  b) at least one neutralizing agent;
  c) from about 1% to about 15% by weight, of at least one organic solvent; and
  d) water;
wherein the pH of the composition is from about 2 to about 6; all weights being relative to the total weight of the composition; and (2) mixing the components u(a) to (d) until uniformly distributed.

In certain embodiments, the compositions in the above described methods further comprise at least one auxiliary ingredient selected from at least one propellant, at least one emulsifier, at least one rheology modifier, at least one film forming polymer other than the film-forming latex polymers, and mixtures thereof.

In other embodiments, the compositions and the compositions in the above described methods are in the form of aqueous hair cosmetic compositions such as liquids, gels, lotions or creams.

In other embodiments, the compositions and the compositions in the above described methods are in the form of sprays. The sprays may be both aerosol and non-aerosol.

In other embodiments, the compositions and the compositions in the above described methods are in the form of hair mousse cosmetic compositions.

In an embodiment, the at least one neutralizer in the compositions of the methods of the present invention is selected from monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof.

In some embodiments, the at least one neutralizing agent in any one of the above-described compositions of the invention is 2-amino-2-methyl-1-propanol.

In certain embodiments, the at least one film-forming latex polymer in any one of the above-described compositions of the invention is fully neutralized.

In an embodiment, the at least one solvent in the compositions of the present invention is monobutyl ether of dipropylene glycol.

In certain embodiments, the cosmetic composition in any one of the above-described methods is for controlling or slowing down the coloration of hair, or for controlling the variation in the artificial color of hair.

The methods according to various exemplary embodiments of the present invention may also provide improved and/or increased ease of uniform color deposit or a more uniform overall hair color from root to ends.

It should be understood that the precise numerical values used in the specification, including the examples and claims, form additional embodiments of the invention, and are intended to include any ranges which can be narrowed to any to end points disclosed within the exemplary ranges and values provided. Efforts have been made to ensure the accuracy of the numerical values disclosed. However, any measured value can inherently contain certain errors resulting from the standard deviation found in its respective measuring technique.

Latex Polymers

According to various exemplary embodiments of the disclosure, the at least one film-forming latex polymer is present in an amount ranging from about 2.5% to about 10% by weight, based on a dry weight basis, relative to the total weight of the composition.

In further embodiments, the at least one film-forming latex polymer, may be used in combination with a second film-forming latex polymer, which may be identified as polymer A and polymer B. Compositions according to certain embodiments may comprise at least one polymer A and at least one polymer B, wherein both polymer A and polymer B are a film-forming latex polymers.

In at least certain exemplary and non-limiting embodiments, latex polymers A and B may be chosen such that polymer A comprises at least one latex polymer which is optionally a film-forming polymer that is a relatively soft, flexible latex polymer, and polymer B comprises at least one latex polymer which is optionally a film-forming polymer that is a relatively hard, brittle polymer, although such characteristics are not required.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface by "at least one film-forming latex polymer," it is contemplated that one or more film-forming latex polymers may be chosen.

In further embodiments, the composition comprises exactly two latex polymers, at least one of which is a film-forming polymer. In yet further embodiments, the composition comprises at least two latex polymers, both of which are film-forming polymers, but does not comprise any additional film-forming latex polymers.

In at least certain embodiments of the disclosure, the at least one film-forming latex polymer are provided in the form of aqueous dispersions prior to formulating the compositions of the disclosure. In various embodiments, the aqueous dispersions may be obtained through an emulsion polymerization of monomers wherein the resulting latex polymers have a particle size lower than about 1 μm. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

Thus, the latex polymers may, in various exemplary embodiments, exist as dispersed polymer particles in a dispersion medium, such as an aqueous dispersion medium. The latex polymers may, in certain embodiments, be dispersed in independent dispersion media. In yet further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the disclosure, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex particles according to the disclosure may have an average diameter ranging up to about 1000 nm, such as from about 50 nm to about 800 nm, or from about 100 nm to about 500 nm. Such particle sizes may be measured with a laser granulometer (e.g. Brookhaven BI90).

In further embodiments, the latex polymers may be chosen from uncharged and charged latex polymers. Thus, the latex polymers may, according to various exemplary embodiments, be chosen from nonionic latex polymers, cationic latex polymers, and anionic latex polymers.

As non-limiting examples of latex polymers that may be used, mention may be made, independently, of acrylate latex polymers and polyurethane latex polymers.

By way of non-limiting example only, the at least one film-forming latex polymer may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl (meth)acrylic, such as, for example, methyl (meth)acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth) acrylic, cyclohexyl (meth)acrylic, isohexyl (meth)acrylic, heptyl (meth)acrylic, isoheptyl (meth)acrylic, octyl (meth) acrylic, isooctyl (meth)acrylic, as well as combinations of any of the above.

The esters of (meth)acrylic monomers may be, by way of non-limiting example, C1-C8 alkyl (meth)acrylates such as methyl (meth)acrylate, ethyl (meth)acrylate, propyl (meth) acrylate, isopropyl (meth)acrylate, butyl (meth)acrylate, tert-butyl (meth)acrylate, pentyl(meth) acrylate, isopentyl (meth) acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth) acrylate, isoheptyl (meth)acrylate, octyl (meth)acrylate, isooctyl (meth)acrylate, allyl (meth)acrylate, and combinations thereof. Additional and non-limiting examples include C1-C8 alkoxy (meth)acrylates, such as methoxy (meth)acrylate, ethoxy (meth)acrylate, propyl oxide (meth)acrylate, iso-propyl oxide (meth)acrylate, butyl oxide (meth)acrylate, tert-butyl oxide (meth)acrylate, pentyl oxide (meth) acrylate, isopentyl oxide (meth)acrylate, neopentyl oxide (meth)acrylate. The esters may be, by way of non-limiting example, C2-C6 hydroxy alkyl (meth)acrylates, such as hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth) acrylate, 1,6,hexane diol di(meth)acrylate, and any combination thereof. The esters may be, by way of non-limiting example, aryl (meth)acrylates such as benzyl (meth)acrylate, phenyl (meth)acrylate, and any combination thereof. The esters can further contain amino groups such as aminoethyl (meth)acrylate, N,N-dimethylaminoethyl (meth)acrylate, N,N-dimethylaminopropyl (meth)acrylate, N, N-dimethylaminodimethylpropyl (meth)acrylate, N,N-diethyleaminoethyl (meth)acrylate, and N,N,N-trimethylaminoethyl (meth) acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth) acrylamides, in particular N—(C1-C12) alkyl (meth)acrylates such as N-ethyl (meth)acrylamide, N-t-butyl (meth) acrylamide, N-t-octyl (meth)acrylamide, N-methylol (meth) acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, Wallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

Silicone acrylic polymers may also optionally be used as vinyl polymer in at least one exemplary and non-limiting embodiment.

In at least certain, non-limiting exemplary embodiments, acrylic latex polymers may be chosen from aqueous dispersions of Methacrylic Acid/Ethyl Acrylate copolymer (INCI: Acrylates Copolymer, such as LUVIFLEX® SOFT by BASF), PEG/PPG-23/6 Dimethicone Citraconate/C10-30 Alkyl PEG-25 Methacrylate/Acrylic Acid/Methacrylic Acid/ Ethyl Acrylate/Trimethylolpropane PEG-15 Triacrylate copolymer (INCI: Polyacrylate-2 Crosspolymer, such as FIXATE SUPERHOLD™ by Lubrizol), Styrene/Acrylic copolymer (such as NEOCRYL® A-1120, DSM), Ethylhexyl Acrylate/Methyl Methacrylate/Butyl Acrylate/Acrylic Acid/ Methacrylic Acid copolymer (INCI: Acrylates/Ethylhexyl Acrylate Copolymer, such as DAITOSOL 5000SJ, Daito Kasei Kogyo), Acrylic/Acrylates Copolymer (INCI name: Acrylates Copolymer, such as DAITOSOL 5000AD, Daito Kasei Kogyo), and Acrylic copolymers and Acrylates Copolymers, such as those known under the tradenames VINYSOL 2140 (Daido Chemical), ACULYN™ 33 (Dow Chemical), LUVIMER® MAE (BASF), or BALANCE CR (AKZO NOBEL).

In yet further exemplary and non-limiting embodiments, the at least one film-forming latex polymer may be chosen from polyurethane latex polymers, such as aqueous polyurethane dispersions comprising the reaction products of (i), (ii), and/or (iii), defined below.

Reaction product (i) may be any prepolymer according to the formula:

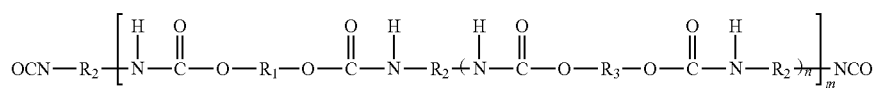

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexane-dicarboxylic, 2,5-norboranedicarboxylic, diglycolic, thiodipropionic, 2,5-naphthalene-dicarboxylic, 2,6-naphthalenedicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythioether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy) diphenyl-dimethylmethane, and (1,6)-hexanediol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylolbutanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

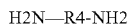

H2N—R4—NH2 wherein R4 is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophoronediamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

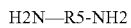

H2N—R5—NH2 wherein R5 is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such latexes include, but are not limited to, aqueous polyurethane dispersions comprising a reaction product of a prepolymer comprising a dihydroxyl compound, a polyisocyanate, and a low molecular weight diol and at least two diamine compounds and wherein the composition is substantially free of triethanolamine stearate such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), aliphatic polyurethane and aliphatic polyester polyurethane (such as the NEOREZ® series, DSM, such as NEOREZ® R989, INCI name: Polycarbamyl Polyglycon Ester).

In at least certain embodiments, the at least one film-forming latex polymer may be chosen from polyacrylic latex, polyacrylate latex, polystyrene latex, polyester latex, polyamide latex, polyurea latex, polyurethane latex, epoxy resin latex, cellulose-acrylate latex, and their copolymers.

In at least certain embodiments, the at least one film-forming latex polymer may be chosen from Acrylates copolymer (ACULYN 33 or LUVIFLEX® SOFT or DAITOSOL 5000AD), Acrylates/Hydroxyesters Acrylates Copolymer (ACUDYNE 180), Polyacrylate-2 Crosspolymer (FIXATE SUPERHOLD™) Styrene/Acrylic copolymer (NEOCRYL® A-1120), Acrylates/Ethylhexyl Acrylate Copolymer (DAITOSOL 5000SJ), Polyurethane-34 (BAYCUSAN® C1000), Polyurethane-34 (BAYCUSAN® C1001), Polyurethane-32 (BAYCUSAN® C1003), Polyurethane-35 (BAYCUSAN® C1004), Polyurethane-48 (BAYCUSAN® C1008), Polyurethane-1 (LUVISET® P.U.R), Polycarbamyl Polyglycon Ester (NEOREZ® R989) and mixtures thereof.

In other embodiments, the at least one film-forming latex polymer comprises both acrylates copolymer and acrylates/hydroxyesters acrylates copolymer.

In various embodiments according to the disclosure, the at least one film-forming latex polymer may be chosen from a polymer that comprises both acrylate and polyurethane parts at the molecular level.

Compositions

As described herein, exemplary compositions according to the disclosure may comprise at least one film-forming latex polymer. In certain embodiments, the at least one film-forming latex polymer is present in an amount ranging from about 2.5% to about 10% by weight, based on a dry weight basis, such as about 2.5% to about 8% by weight, based on a dry weight basis, such as about 2.75% to about 6% by weight, based on a dry weight basis, such as about 3% to about 5.5% by weight, based on a dry weight basis, or about 3% to about 5% by weight, based on a dry weight basis, relative to the total weight of the composition, including all ranges and subranges there between.

In some embodiments, the at least two film-forming latex polymers are present in the compositions of the invention.

In certain embodiments, when there are at least two film-forming latex polymers in the compositions of the invention, the film-forming latex polymers are present in a combined amount ranging from about 2.5% to about 10% by weight, based on a dry weight basis, such as about 2.5% to about 8% by weight, based on a dry weight basis, such as about 2.75% to about 6% by weight, based on a dry weight basis, such as about 3% to about 5.5% by weight, based on a dry weight basis, or about 3% to about 5% by weight, based on a dry weight basis, relative to the weight of the composition, including all ranges and subranges there between. By way of non-limiting example, the combined amount of latex polymers may be about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10%, by weight, based on a dry weight basis, relative to the total weight of the composition.

In at least one exemplary embodiment, the combined amount of film-forming latex polymers is less than about 10% by weight, based on a dry weight basis, such as less than about 5% by weight, based on a dry weight basis, relative to the total weight of the composition.

Neutralizing Agent

The at least one film-forming latex of the present invention is preferably employed in a neutralized form. In preferred embodiments, the at least one film-forming latex polymer of the present invention is neutralized in water or in an aqueous solution with a neutralizing agent before the polymer is added into the pretreatment composition of the present invention.

In other preferred embodiments, the at least one film-forming latex polymer of the present invention is neutralized with a neutralizing agent at the time of addition of the polymer into the pretreatment composition of the present invention.

The neutralizing agent is employed in an amount sufficient to neutralize the film-forming latex polymer of the present invention. After neutralization, the film-forming latex polymer is fully neutralized. One indication of neutralization is the clarity of the solution.

Suitable neutralizing agents are other than the at least one salt described above and may be selected from alkali metal carbonates, alkali metal phosphates, organic amines, hydroxide base compounds, and mixtures thereof, particularly from ethylamines, ethyleneamines, alkanolamines, cyclic amines and other cyclic compounds, saturated or unsaturated, having one or more nitrogen atoms within the ring.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical.

Organic amines may also be chosen from alkanolamines such as mono-, di- or trialkanolamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Other examples include but are not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Amino acids that may be used in the present disclosure include but are not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

Further as non-limiting examples, the amino acids may be chosen from basic amino acids comprising an additional amine function optionally included in a ring or in a ureido function. Such basic amino acids may be chosen from histidine, lysine, arginine, ornithine, and citrulline.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

The alkali metal phosphates and carbonates that may be used are, for example, sodium phosphate, potassium phosphate, sodium carbonate, sodium bicarbonate, potassium carbonate, potassium bicarbonate, and their derivatives.

The hydroxide base compounds chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

According to at least one embodiment, the neutralizing agent is chosen from at least one organic amine such as at least one alkanolamine. Particularly preferred alkanolamines are ethanolamine (also known as monoethanolamine or MEA), triethanolamine, and 2-amino-2-methyl-1-propanol, and mixtures thereof. An even more particularly preferred alkanolamine is 2-amino-2-methyl-1-propanol.

The at least one neutralizing agent of the present invention may be employed in an amount of from about 0.01% to about 10% by weight, or such as from about 0.01% to about 5% by weight, or such as from about 0.1% to about 3% by weight, based on the total weight of the cosmetic composition of the present invention.

In preferred embodiments, the at least one neutralizing agent of the present invention may be employed in an amount of from about 0.01% to about 2% by weight, or preferably from about 0.1% to about 1% by weight, based on the total weight of the cosmetic composition of the present invention.

Organic Solvents

The compositions of the present invention comprise at least one organic solvent.

Suitable organic solvents may be chosen from volatile and nonvolatile organic solvents.

Suitable organic solvents are typically C1-04 lower alcohols, glycols, polyols, polyol ethers, hydrocarbons, and oils. Examples of organic solvents include, but are not limited to: ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycol-monobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, polybutene, hydrogenated polyisobutene, hydrogenated polydecene, polydecene, squalene, petrolatum and iso-paraffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity 9 centistokes (8×10-6 m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluro oils such as nonafluoromethoxybutane and perfluoro-methylcyclopentane.

The amount of the organic solvent/compound present in the compositions of the present invention can range from about 0.5% to about 60%, or from about 0.5% to about 40%, or from about 0.5% to about 30%, or from about 1% to about 20%, and in some embodiments, from about 1% to about 15%, by weight, or preferably from about 1% to about 10%, by weight, or more preferably from about 1.5% to about 8%, by weight, or from about 3% to about 8%, by weight, including all ranges and subranges there-between, relative to the total weight of the composition.

In some embodiments, the amount of the organic solvent/compound present in the compositions of the present invention is at about 2%, about 2.5%, about 3%, about 3.5%, about 4%, about 4.5%, about 5%, about 5.5% about 6%, about 6.5%, about 7%, about 7.5% or about 8% by weight, including all ranges and subranges there-between, relative to the total weight of the composition.

In certain embodiments, compositions of the present invention comprise both water and organic solvents/compounds selected from volatile organic solvents, non-volatile organic solvents, and mixtures thereof.

Preferred examples of organic solvents/compounds include volatile organic solvents such as C2 to C4 monoalcohols, such as ethanol, isopropyl alcohol, butanol, polyols such as C2-C6 glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof. In certain embodiments, it is preferred that the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In other embodiments, it is preferred that the amount of volatile organic solvent/compound does not exceed 8% by weight, relative to the weight of the composition of the present invention.

In preferred embodiments, the amount of volatile organic solvent/compound does not exceed 6% by weight, relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures, thereof.

In certain embodiments, it is preferred that the amount of nonvolatile organic solvent/compound does not exceed 40% by weight, relative to the weight of the composition of the present invention.

In other certain embodiments, it is preferred that the amount of nonvolatile organic solvent/compound does not exceed 20% by weight, relative to the weight of the composition of the present invention.

In yet other certain embodiments, it is preferred that the amount of nonvolatile organic solvent/compound does not exceed 10% by weight, relative to the weight of the composition of the present invention.

In preferred embodiments of the present invention, the at least one organic solvent is chosen from ethanol, glycol ether, for example, dipropylene glycol n-butyl ether, known under the tradename of DOWANOL DPnB, isododecane, mineral oil, propylene glycol, pentylene glycol, hexylene glycol, glycerol, and mixtures thereof.

In certain embodiments of the present invention, the at least one organic solvent is chosen from ethanol.

The organic solvents may also comprise the solvent of the dispersion medium employed to disperse the latex polymers and silicone organic polymer compound of the present invention.

In yet some other embodiments, water that is not added as a separate ingredient, by itself, into the compositions of the present invention, such that water is present in the compositions of the present invention when it accompanies one or more ingredients of a raw material that is added into the composition invention.

Water

The compositions of the present invention contain water. Water can be present in the amount of about 95%, 90%, 80%, 70%, 60%, 50%, 40%, 30%, 20%, 10%, 5% by weight or less, relative the total weight of the compositions. Additionally, water can be present in the compositions of the present invention in the amount of from about 20% to about 95% by weight, or from about 50% to about 92% by weight, or from about 50% to about 90% by weight, or from about 60% to about 80% by weight, relative to the weight of the compositions.

In other embodiments, water can be present in the compositions of the present invention in the amount of at least about 95%, 90%, 80%, 70%, 60%, 50%, 40%, 30%, 20%, 10%, 5% by weight or less, relative to the total weight of the compositions.

pH

In some embodiments, the pH of the compositions employed in the methods of the present invention ranges from about 2 to about 6, or preferably from about 3 to about 6, or more preferably from about 4 to about 6, including all ranges and subranges there between.

In certain embodiments, the pH of the compositions employed in the methods of the present invention is at about 5.3.

The pH of the composition of the present invention may be adjusted to the desired value using the at least one neutralizing agent of the present invention and/or other conventional acidifying or basifying agents.

All numbers expressing pH values are to be understood as being modified in all instances by the term "about" which encompasses up to +/−3%.

Auxiliary Ingredients

The compositions of the present invention can also comprise auxiliary ingredients, for instance those chosen from the non-exhaustive list such as propellants, emulsifiers, rheology modifiers and film forming agents such as film forming polymers other than the latex polymers of the invention, non-film forming polymers, humectants, conditioning agents, plasticizers, coalescers, fillers, dyes such as oxidative dyes and direct dyes, waxes, surfactants, preserving agents, oils such as mineral, organic or plant oils, fragrances, antioxidants, sunscreens, sequestering agents, softeners, antifoams, basifying agents, wetting agents, spreading agents, dispersants, pigments, proteins, ceramides, vitamins, clays, colloidal minerals, nacreous agents, peptizers, preserving agents, reducing agents, oxidizing agents, pH adjusters, silicones, plant extracts, paraffins, fatty acids, and mixtures thereof.

The person skilled in the art will ensure that any auxiliary ingredient and their amounts are selected in such a way as to cause no detriment to the properties of the compositions disclosed herein.

The at least one auxiliary ingredient may be present in an amount ranging from 0.001% to 50% by weight, relative to the total weight of the entire composition, including all ranges and subranges there between.

In some embodiments, the compositions of the present invention may contain at least one film forming polymer chosen from all the anionic, cationic, amphoteric and nonionic film forming polymers and mixtures thereof In certain embodiments, the compositions of the present invention may contain at least one emulsifier.

Emulsifiers or dispersing agents, include, without limitation, any which are compatible with the solvent and ingredients used in the composition of the present invention. The emulsifying agents which can be used according to the invention are those having an HLB of less than 7 and in particular fatty acid esters of polyols such as mono-, di-, tri- or sesquioleates or -stearates of sorbitol or glycerol, laurates of glycerol or polethylene glycol; alkyl or alkoxy dimethicone copolyols having an alkyl or alkoxy chain pendent or at the end of a silicone-based backbone having for example from 6 to 22 carbon atoms. The emulsifying agents may also be those having an HLB greater than 7 such as fatty acid esters of polyethylene glycol (monostearate or monolaurate of polyethylene glycol); esters of fatty acids (stearate, oleate) of sorbitol which are polyoxyethylenated; polyoxy ethylenated alkyl (lauryl, cetyl, stearyl, octyl)ethers and dimethicone copolyols. In general, it is possible to use nonionic or anionic or cationic emulsifiers well known to persons skilled in the art.

The nonionic type emulsifiers are fatty acids or amides of polyalkoxylated and/or polyglycerolated fatty acids; polyoxyethylenated and/or polyoxypropylenated fatty alcohols (i.e., compounds prepared by reacting an aliphatic fatty alcohol such as behenyl or cetyl alcohol with ethylene oxide or propylene oxide or an ethylene oxide/propylene oxide mixture); fatty acid esters of polyols, optionally polyoxyethylenated and/or polyoxypropylenated (i.e., compounds prepared by reacting a fatty acid such as stearic acid or oleic acid with a polyol such as, for example, an alkylene glycol or glycerol or a polyglycerol, optionally in the presence of ethylene oxide or propylene oxide or an ethylene oxide/propylene oxide mixture); and polyalkoxylated and/or polyglycerolated alkylphenols; or polyalkoxylated and/or polyglycerolated 1,2- or 1,3-alkanediols; and alkylethers of polyalkoxylated and/or polyglycerolated 1,2- or 1,3-alkanediols or alkenediols, or mixtures thereof.

The esters of fatty acids and polyoxyethylenated polyols for which the polyol is sorbitol are known products (Polysorbate and products sold under the mark "Tween").

The emulsifiers according to the invention can also be anionic surfactants which may have a hydrophilic-lipophilic balance (HLB) ranging from 10 to 40. They are principally salts of fatty acids (for example alkaline salts or organic salts such as amine salts), the said fatty acids having, for example, from 12 to 18 carbon atoms and being able to have a double bond as in the case of oleic acid; the alkaline salts or salts of organic bases of alkyl-sulfuric and alkyl-sulfonic acids having 12 to 18 carbon atoms, of alkyl-arylsulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene. All these anionic surfactants are well known and many among them are commercial products.

The emulsifiers according to the invention can also be cationic surfactants such as quaternary ammonium derivatives.

Particularly preferred emulsifying agents are Isoceteth-20, Polysorbate 20, PEG-40 hydrogenated castor oil, oleth-2, laureth-7, cetyl alcohol, glyceryl stearate, and mixtures thereof.

The emulsifiers may be present in the composition of the present invention in an amount of from 0.05% to 10% by weight, preferably in an amount of from 0.1 percent to 5% by weight, and more preferably in an amount of from 0.5% to 3.0% by weight, based on the total weight of the composition.

The emulsifiers may be employed in the compositions of the present invention in order to solubilize fatty substances such as fragrance oils or esters, whenever said fatty substances are additionally present in the compositions.

In other embodiments, the compositions of the present invention may contain at least one rheology modifier (also called rheology-modifying agent).

Broadly, the rheology modifier(s) that may be useful in the practice of the present invention include those conventionally used in cosmetics such as polymers of natural origin and synthetic polymers. Rheology modifiers are employed in the compositions of the present invention when it is desired to adjust the viscosity or thickness of the compositions or to achieve a particular composition texture.

Representative rheology-modifying agents that may be used in the practice of the present invention are those other than the at least one film forming polymer of the present invention and include nonionic, anionic, cationic, and amphoteric polymers, and other rheology modifiers such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, crosslinked homopolymers of acrylic acid or of acrylamidopropane-sulfonic acid, associative polymers, non-associative thickening polymers, and water-soluble thickening polymers.

In some embodiments, the rheology-modifying agent includes a polymer other than the at least one film forming polymer of the present invention and chosen from nonionic, anionic, cationic and amphoteric amphiphilic polymers.

The rheology-modifying agents may also be chosen from associative celluloses include quaternized cationic celluloses and quaternized cationic hydroxyethylcelluloses modified by groups containing at least one hydrophobic chain, such as alkyl, arylalkyl or alkylaryl groups containing at least 8 carbon atoms, and mixtures thereof.

The alkyl radicals carried by the above quaternized celluloses or hydroxyethylcelluloses may, in various embodiments, comprise from 8 to 30 carbon atoms. The aryl radicals may, for example, denote the phenyl, benzyl, naphthyl or anthryl groups. Representative examples of quaternized alkylhydroxy-ethylcelluloses containing a C8-C30 hydrophobic chain include the products Quatrisoft LM 200®, Quatrisoft LM-X 529-18-A®, Quatrisoft LM-X 529-18B® (C12 alkyl) and Quatrisoft LM-X 529-8® (Ci8 alkyl) sold by Amerchol and the products Crodacel QM®, Crodacel QL® (C12 alkyl) and Crodacel QS® (Ci8 alkyl) sold by Croda.

Representative examples of nonionic cellulose derivatives include hydroxyethylcelluloses modified by groups comprising at least one hydrophobic chain, such as alkyl, arylalkyl or alkylaryl groups, or their blends, and in which the alkyl groups are, for example, C8-C22 alkyl groups, such as the product Natrosol Plus Grade 330 CS® (C16 alkyls) sold by Aqualon or the product Bermocoll EHM 100® sold by Berol Nobel.

Representative examples of cellulose derivatives modified by alkylphenyl polyalkylene glycol ether groups include the product Amercell Polymer HM-1500® sold by Amerchol.

The rheology-modifying agent is typically present in an amount ranging from about 0.01% to about 10% by weight, in some embodiments from about 0.1% to about 5% by weight, or from about 0.5% to about 1% by weight, based on the total weight of the composition.

In some instances, certain rheology modifiers are also known as gelling agents or thickening agents.

In yet other embodiments, the compositions of the present invention may contain at least one propellant. Propellants can used to deliver the composition as a foam (such as in a mousse or foam product).

Representative examples of propellants include C3 to C5 alkanes such as n-butane, isobutane, isopropane, and propane, dimethyl ether, C2-C5 halogenated hydrocarbons, e.g., 1,1-difluoroethane or hydroflurocarbon, difluoroethane, chlorodifluoroethane, chlorodifluoromethane, air (such as compressed air), nitrogen, carbon dioxide, and mixtures thereof. The amount of the propellant can range from about 3 to about 90%, and in some embodiments from about 3 to about 60%, by weight, or such as from about 3 to about 20% by weight, or such as from about 3 to about 10% by weight, or such as from about 3 to about 6%, by weight based on the total weight of the composition, including all ranges and subranges there between.

The compositions in the methods of the present invention may take the form of a gel, a mousse such as an aerosol mousse, a spray such as an aerosol spray or a pump spray, a spray gel, a lotion, a tonic, or a cream. The compositions may also be provided as rinse-off or leave-in products, preferably, rinse-off products.

In one particular embodiment, the composition of the present invention is in the form of a cream.

In another particular embodiment, the composition of the present invention additionally contains at least one propellant and is in the form of a mousse.

In some other embodiments, the cosmetically acceptable carrier in the composition of the present invention comprises at least one volatile organic solvent or compound (VOC) (e.g., in the case of a spray or an aerosol spray). To reduce the amount of VOC (low VOC product), the volatile organic solvent or compound is partially replaced with water. The amount of the volatile organic solvent generally ranges from greater than 0 (e.g., about 0.01%) to about 90%, and in some embodiments from greater than 0 to about 55%, and in some embodiments from greater than 0 to about 2%, by weight, based on the total weight of the composition. It is preferred that the amount of volatile organic solvent does not exceed 55% by weight.

The compositions of the present invention may be packaged, for example, in a bottle, a spray device such as an aerosol container/can, a pump dispenser or pump spray, a jar, such as those customary in cosmetology.

The compositions may be applied onto keratin fibers by using the fingers or hand, or by use of a suitable applicator or by directly dispensing the compositions from a device.

Method of Making

The compositions of the present invention are made by combining at least one film-forming latex polymer, at least one neutralizing agent, at least one organic solvent and water.

In one embodiment, the method of making the acidic pretreatment composition of the present invention comprises the steps of:
(1) combining
 a) from about 2.5% to about 10% by weight, based on a dry weight basis, of at least one film-forming latex polymer.
 b) at least one neutralizing agent;
 c) from about 1% to about 20% by weight, of at least one organic solvent; and
 d) water;
wherein the pH of the composition is from about 2 to about 6; all weights being relative to the total weight of the composition; and
(2) mixing the foregoing components in (1) until uniformly distributed.

The at least one neutralizing in the above-described methods of making may be employed in an amount sufficient to fully neutralize the at least one film-forming latex polymer.

In an embodiment, the at least one film-forming latex polymer is first combined with an amount of the at least one neutralizing agent sufficient to fully neutralize the film-forming latex polymer. The fully neutralized latex polymer is then combined with one or more of the rest of the ingredients of the pretreatment composition of the invention.

Method of Use

Embodiments disclosed herein are methods for coloring the hair, or for controlling/slowing down the coloration of hair or controlling the variation in the artificial color of hair, or kits or systems thereof, involving applying onto hair, any one of the compositions disclosed herein.

The compositions of the present invention may be employed in an effective amount to adequately cover the surface of the selected or isolated fibers of the hair and to achieve the desired cosmetic effect such as uniform hair color from root to tip, multi-toned or multi-colored hair, highlights, lowlights, or satisfactory gray coverage. The precise amount of composition to be applied onto the hair will thus depend on the degree of treatment desired.

Thus, in one embodiment, the present invention relates to a method of coloring hair, said method comprising:
(1) applying onto hair, an acidic pretreatment hair composition comprising:
 a) from about 2.5% to about 10% by weight, based on a dry weight basis, of at least one film-forming latex polymer;
 b) at least one neutralizing agent;
 c) from about 1% to about 20% by weight, at least one organic solvent; and
 d) water;
wherein the pH of the composition is from about 2 to about 6; all weights being relative to the total weight of the composition; and
(2) applying onto the hair, a hair color altering composition.

In another embodiment, the present invention relates to a method for slowing down the coloration of hair, the method comprising:
(1) applying onto hair, an acidic pretreatment hair composition, comprising:
 a) from about 3% to about 5% by weight, based on a dry weight basis, of acrylates copolymer, acrylates/hydroxyesters acrylates copolymer and mixtures thereof;
 b) from about 0.1% to about 1% by weight of 2-amino-2-methyl-1-propanol;
 c) from about 3% to about 8% by weight of at least one organic solvent selected from ethylene glycol monopropyl ether, ethylene glycol monobutyl ether, propylene glycol monomethyl ether, propylene glycol monopropyl ether, propylene glycol monobutyl ether, diethylene glycol monoethyl ether, diethylene glycol monobutyl ether, dipropylene glycol n-butyl ether, and mixtures thereof; and d) water;

wherein the pH of the composition is from about 2 to about 6; all weights being relative to the total weight of the composition; and (2) applying onto the hair, a hair color altering composition.

In a third embodiment, the present invention relates to a method for controlling the variation in the artificial color of hair, the method comprising:

(1) applying onto the mid-shaft up to the ends of the hair, an acidic pretreatment hair composition, comprising:

a) from about 2.5% to about 8% by weight, based on a dry weight basis, of acrylates copolymer, acrylates/hydroxyesters acrylates copolymer and mixtures thereof;

b) from about 0.01% to about 5% by weight of at least one neutralizing agent selected from monoethanolamine, 2-amino-2-methyl-1-propanol, 2-amino-2-methyl-1,3-propanediol, 3-amino-1,2-propanediol, 3-dimethylamino-1,2-propanediol, and mixtures thereof;

c) from about 1% to about 10% by weight of at least one organic solvent; and d) water;

wherein the pH of the composition is from about 2 to about 6; all weights being relative to the total weight of the composition; and (2) applying onto the roots up to the ends of the hair, a hair color altering composition.

The hair color altering composition that may be applied after contacting the hair with the pretreatment composition comprises at least one color-altering agent selected from oxidative dyes, direct dyes, couplers, oxidation dye precursors, pigments, lightening agents, lifting agents, bleaching agents, oxidizing agents, and mixtures thereof.

Thus, the hair color altering composition may be a permanent hair dye product, a semi-permanent hair dye product, a demi-permanent hair dye product, a bleach product, a temporary dye product, or a hair lightening or highlighting product.

The hair color altering composition may first be combined with a developer or oxidizing composition containing at least one oxidizing agent before application onto the hair.

Instructions for applying the compositions disclosed herein may comprise directions of use of the composition for the end-user to follow. The end-user may be a consumer or cosmetologist or salon hair dresser. Directions may comprise instructing the end-user to take an amount of the composition in sufficient quantity such that the composition adequately covers the selected hair fibers and imparts the desired color or tone to the hair fibers. Directions may also comprise instructing the end-user to apply the pretreatment composition from mid-shaft of the hair or from the visible demarcation line between new hair growth and previously artifically colored hair down to the ends/tips of the hair. Directions may additionally instruct the end-user to use a device such as a foil, comb, brush (e.g., hair color brush or brush wand), flat iron plates or the fingers for separating the fibers of the hair.

It has been surprisingly and unexpectedly discovered that the methods of the present invention resulted in a uniform overall color from root to tip of the hair, as well as satisfactory gray coverage. The pretreatment composition is also beneficial for multi-toned or multi-colored hair, highlight or lowlight treatments.

The efficacy of the pretreatment compositions on the hair may be evaluated by assessing (whether visually or by a measuring device) the appearance and color of the hair after contacting the hair with the pretreatment composition of the invention, followed by application of a hair color altering composition onto the hair, rinsing both compositions and allowing the hair to dry naturally or drying the hair with a blow dryer.

As used herein, the method and composition disclosed herein may be used on the hair that has not been artificially dyed, pigmented or permed or on the hair that has been artificially dyed, pigmented or permed.

EXAMPLES

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

The following Examples are intended to be non-restrictive and explanatory only, with the scope of the invention being defined by the claims.

The ingredient amounts/concentrations in the compositions/formulas described below are expressed in % by weight, based on the total weight of the composition/formula.

Example 1

TABLE 1

Inventive Composition - Formula A

| Raw Material/INCI name | Uses | Amount |
| --- | --- | --- |
| STEARTH-20 | Emulsifiser | 2.000 |
| C30-45 ALKYLDIMETHYLSILYL POLYPROPYLSILSESQUIOXANE | Wax Resin | 1.994 |
| MINERAL OIL | Lubricant | 7.000 |
| ACRYLATES/C10-30 ALKYL ACRYLATE CROSSPOLYMER | Emulsifier | 0.500 |
| AMINOMETHYL PROPANOL | Neutralizing Agent | 0.300 |
| EDTA | Chelating Agent | 0.20 |
| PHENOXYETHANOL | Preservative | 0.150 |
| PPG-2 BUTYL ETHER | Solvent | 5.000 |
| ACRYLATES/HYDROXYESTERS ACRYLATES COPOLYMER * | Latex polymer | 1.89 Active |
| ACRYLATES COPOLYMER ** | Latex polymer | 1.4 Active |
| WATER | Solvent | QS |
| | TOTAL: | 100.00 |
| | PH: | 5.31 |

* ACUDYNE 180 (DOW CHEMICAL) -
** ACULYN 33 ™ (DOW CHEMICAL)

The formula above was made according to this method of preparation:

1. Add stearth-20, C30-45 alkyldimethylsilyl polypropylsilsesquioxane and mineral oil together to form Phase A and heat to 80° C.
2. Heat water between 60-80° C. Add acrylates/C10-30 alkyl acrylate crosspolymer and begin mixing with chopper blade at 250 RPM until dispersed. Add in ½ of aminomethyl propanol to mixture to form Phase B. Solution will become clear. Continue mixing for 20 minutes.
3. Using Homogenizer Blade at 600-800 RPM, add Phase A to Phase B. Mix for 20 minutes, sidesweeping continuously.
4. Switch to chopper blade. Mix between 200-300 RPM for 10 minutes.

5. Add ½ of PPG-2 butyl ether to resulting mixture. Sidesweep mixture and increase mixing speed to 400-600 RPM. Mix for 10 minutes.
6. Add acrylates/hydroxyesters acrylates copolymer to mixture. Sidesweep mixture and increase mixing speed to 800 RPM. Mix for 10 minutes.
7. Add remainder of aminomethyl propanol to mixture.
8. Add remainder of PPG-2 butyl ether to mixture. Continue mixing for 10 minutes at 300-500 RPM.
9. Add phenoxyethanol. Continue mixing for 10 minutes at 300-500 RPM.
10. Add EDTA. Continue mixing for 10 minutes at 100-200 RPM.
11. QS with water.

Example 2

Colorimetric Measurements for Color Deposit on Hair Swatches

The Minolta CM2600d spectrocolorimeter (specular components included, 10 degrees angle, illuminant D65) in the CIEL*a*b* system was used for measuring the degree of color deposit on hair, Thus, the L parameter L was measured. L* represents the intensity of the color. The greater the value of L, the lighter or less intense the color. Conversely, the lower the value of L, the darker or more intense the color (this can also indicate greater color deposit when the composition contains colorants).

ΔL or the difference between the L value for the treated hair versus the L value for the control hair swatch can also be measured. ΔL represents a change in the value of L: the more negative the ΔL value is, the darker the color that is deposited on the hair: ΔL=Lt (treated hair)−Lc (control hair).

COMPARATIVE EXAMPLES

TABLE 2

Comparative Examples on Unpermed Hair

| Comparative Examples | Shade | 90% Gray Hair Type | L* |
| --- | --- | --- | --- |
| Example 1 Control | Virgin hair | Unpermed | 59.96 |
| Example 2 | Chromatics 6.54 brown/copper | Unpermed | 25.02 |
| Example 3 | Pref. 6.45 auburn | Unpermed | 23.49 |
| Example 4 | Pref. 4R dark auburn | Unpermed | 24.68 |

TABLE 3

Comparative Examples of Permed Hair

| Comparative Examples | Shade | 90% Gray Hair Type | L* |
| --- | --- | --- | --- |
| Example 5 Control | Virgin | Permed | 59.96 |
| Example 6 | Chromatics 6.54 brown/copper | Permed | 21.23 |
| Example 7 | Pref. 6.45 auburn | Permed | 24.56 |
| Example 8 | Pref. 4R dark auburn | Permed | 26.14 |

The above described Comparative Examples 2-4 are hair swatches that were colored using a standard (typical) hair color on unpermed hair, without pre-treating the hair with the inventive composition. Comparative Examples 6-8 are hair swatches that were permed and then colored using a standard (typical) hair color, without pre-treating the hair with the inventive composition. Comparative Example 1 is unpermed hair which has not been colored and which was not pre-treated with the inventive composition. Comparative Example 5 is permed hair which has not been colored and which was not pre-treated with the inventive composition.

TABLE 4

Inventive Composition on Unpermed Hair

| Inventive Examples | Shade | 90% Gray Hair Type | L* |
| --- | --- | --- | --- |
| Example 1 Control | Virgin | Unpermed | 57.77 |
| Example 2 | Chromatics 6.54 brown/copper | Unpermed | 34.59 |
| Example 3 | Pref. 6.45 auburn | Unpermed | 37.95 |
| Example 4 | Pref. 4R dark auburn | Unpermed | 38.35 |

TABLE 5

Inventive Composition on Permed Hair

| | Shade | 90% Gray Hair Type | L* |
| --- | --- | --- | --- |
| Inventive Example 5 control | Virgin | Permed | 57.77 |
| Inventive Example 6 | Chromatics 6.54-brown/copper | Permed | 35.23 |
| Inventive Example 7 | Pref. 6.45 auburn | Permed | 37.25 |
| Inventive Example 8 | Pref. 4R dark auburn | Permed | 38.14 |

The above described Inventive Examples 2-4 are hair swatches that were colored using a standard (typical) hair color on unpermed hair, after applying the inventive composition of Formula A onto the hair. Inventive Examples 6-8 are hair swatches that were permed and then colored using a standard (typical) hair color, after applying the inventive composition of Formula A onto the hair. Inventive Example 1 is unpermed hair which has not been colored but was contacted/treated with the inventive composition of Formula A. Inventive Example 5 is permed hair which has not been colored but was contacted/treated with the inventive composition of Formula A.

Testing Parameters:

This test was conducted on a model with medium length natural level 6 hair color with approximately 50-75% gray hair. Her hair was divided into two sections. The left section contains the Pre-Treatment and the right section does not. The inventive compositions above tested by:

1. Apply 10 g of the inventive composition to the hair, application starting mid-shaft and going to the ends. Allow to process for 10 minutes. Do not rinse off.
2. Apply hair color product on top of inventive composition. Allow to process for 30 minutes.
3. Rinse out both the inventive composition and hair color product.

Observations:

After processing time was completed, both the hair color product and the inventive pretreatment composition were rinsed off model and hair was dried. The model was then taken to the light room for color evaluation. Evaluation showed that the section that contained the inventive pretreatment composition was visibly uniform in color from roots to ends. This section looked more natural and was rich in color. The half of the head that did not contain the inventive pretreatment composition appeared over-processed and faded; especially the mid shaft and ends. Color Deposit was not uniform from roots to ends on the half of the head that did not contain the inventive pretreatment of the present invention.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

What is claimed is:

1. An acidic hair pretreatment composition, comprising:
   a) from about 2.5% to about 10% by weight, based on a dry weight basis, of at least one film-forming latex polymer;
   b) at least one neutralizing agent;
   c) from about 1% to about 20% by weight, of at least one organic solvent; and
   d) water;
   wherein the pH of the composition is from about 2 to about 6;
   all weights being relative to the total weight of the composition;
   with the proviso that the composition does not include a dye.

2. The hair pretreatment composition of claim 1, wherein the at least one film-forming latex polymer (a) is selected from acrylate latex polymers, polyurethane latex polymers, and mixtures thereof.

3. The hair pretreatment composition of claim 2, wherein the at least one film-forming latex polymer (a) is selected from Acrylates copolymer, Acrylates/Hydroxyesters Acrylates Copolymer, Polyacrylate-2 Crosspolymer, Styrene/Acrylic copolymer, Acrylates/Ethylhexyl Acrylate Copolymer, Polyurethane-34, Polyurethane-34, Polyurethane-32, Polyurethane-35, Polyurethane-48, Polyurethane-1, Polycarbamyl Polyglycon Ester and mixtures thereof.

4. The hair pretreatment composition of claim 2, wherein the at least one film-forming latex polymer is fully neutralized.

5. The hair pretreatment composition of claim 4, wherein the at least one film-forming latex polymer (a) is present in an amount of from about 3% to about 5% by weight, relative to the total weight of the composition.

6. The hair pretreatment composition of claim 5, wherein the at least one neutralizing agent (b) is selected from monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof.

7. The hair pretreatment composition of claim 6, wherein the at least one neutralizing agent (b) is present in an amount of from about 0.01% to about 5% by weight, relative to the total weight of the composition.

8. The hair pretreatment composition of claim 7, wherein the at least one organic solvent (c) is chosen from volatile and non-volatile organic solvents.

9. The hair pretreatment composition of claim 8, wherein the at least one organic solvent (c) is selected from ethanol, isopropyl alcohol, butanol, propylene glycol, butylene glycol, pentylene glycol, hexylene glycol, glycerol, isododecane, acetone, propylene carbonate, benzyl alcohol, mineral oil, polybutene, hydrogenated polyisobutene, hydrogenated polydecene, polydecene, squalene, petrolatum, ethylene glycol monomethyl ether, ethylene glycol monopropyl ether, ethylene glycol monobutyl ether, propylene glycol monomethyl ether, propylene glycol monopropyl ether, propylene glycol monobutyl ether, diethylene glycol monoethyl ether, diethylene glycol monobutyl ether, dipropylene glycol n-butyl ether, and mixtures thereof.

10. The hair pretreatment composition of claim 9, wherein the at least one organic solvent (c) is present in an amount of from about 3% to about 8% by weight, relative to the total weight of the composition.

11. The hair pretreatment composition of claim 10, wherein the water (d) is present in an amount of from about 50% to about 92% by weight, relative to the total weight of the composition.

12. The hair pretreatment composition of claim 2, wherein the at least one film-forming latex polymer (a) comprises acrylates copolymer and acrylates/hydroxyesters acrylates copolymer.

13. The hair pretreatment composition of claim 11, wherein the composition is a pretreatment composition for use before applying a hair color-altering composition comprising a color-altering agent selected from oxidative dyes, direct dyes, couplers, oxidation dye precursors, pigments, lightening agents, lifting agents, bleaching agents, oxidizing agents, and mixtures thereof.

14. The hair pretreatment composition of claim 11, wherein the composition is employed for controlling coloration of hair or alteration of the color of hair.

15. The hair pretreatment composition of claim 11, wherein the composition further comprises at least one auxiliary ingredient selected from propellants, emulsifiers, rheology modifiers, film forming agents other than the latex polymer (a), humectants, conditioning agents, plasticizers, coalescers, fillers, waxes, surfactants, preserving agents, oils, fragrances, antioxidants, sunscreens, sequestering agents, softeners, antifoams, basifying agents, wetting agents, spreading agents, dispersants, pigments, proteins, ceramides, vitamins, clays, colloidal minerals, nacreous agents, peptizers, preserving agents, reducing agents, oxidizing agents, pH adjusters, silicones, plant extracts, paraffins, fatty acids, and mixtures thereof.

16. A method of coloring hair, said method comprising:
   (1) applying onto hair, an acidic hair pretreatment composition comprising:
      a) from about 2.5% to about 10% by weight, based on a dry weight basis, of at least one film-forming latex polymer;
      b) at least one neutralizing agent;
      c) from about 1% to about 20% by weight, of at least one organic solvent; and
      d) water;
      wherein the pH of the composition is from about 2 to about 6;
      all weights being relative to the total weight of the composition; and
   (2) applying onto the hair, a hair color altering composition.

17. The method of claim 16, wherein the hair pretreatment composition applied in step (1) is left on the hair for a period of from about 1 minute to about 60 minutes.

18. The method of claim 17, wherein the method is for controlling or slowing down the coloration of hair.

19. The method of claim 18, wherein the hair pretreatment composition applied in step (1) is not rinsed off from the hair before step (2).

20. An acidic hair pretreatment composition for controlling or slowing down the coloration of hair, the composition comprising:
- a) from about 2.5% to about 8% by weight, based on a dry weight basis, of acrylates copolymer, acrylates/hydroxyesters acrylates copolymer and mixtures thereof;
- b) from about 0.1% to about 1% by weight of at least one neutralizing agent selected from monoethanolamine, 2-amino-2-methyl-1-propanol, 2-amino-2-methyl-1,3-propanediol, 3-amino-1,2-propanediol, 3-dimethylamino-1,2-propanediol, and mixtures thereof;
- c) from about 1% to about 10% by weight of at least one organic solvent selected from ethylene glycol monopropyl ether, ethylene glycol monobutyl ether, propylene glycol monomethyl ether, propylene glycol monopropyl ether, propylene glycol monobutyl ether, diethylene glycol monoethyl ether, diethylene glycol monobutyl ether, dipropylene glycol n-butyl ether, and mixtures thereof; and
- d) water;

wherein the pH of the composition is from about 2 to about 6;

all weights being relative to the total weight of the composition;

with the proviso that the composition does not include a dye.

21. A method for controlling or slowing down the coloration of hair, the method comprising: (1) applying onto hair, an acidic pretreatment composition, comprising:
- a) from about 2.5% to about 8% by weight, based on a dry weight basis, of acrylates copolymer, acrylates/hydroxyesters acrylates copolymer, and mixtures thereof;
- b) from about 0.01% to about 5% by weight of at least one neutralizing agent selected from monoethanolamine, 2-amino-2-methyl-1-propanol, 2-amino-2-methyl-1,3-propanediol, 3-amino-1,2-propanediol, 3-dimethylamino-1,2-propanediol, and mixtures thereof;
- e) from about 1% to about 10% by weight of at least one organic solvent selected from ethylene glycol monopropyl ether, ethylene glycol monobutyl ether, propylene glycol monomethyl ether, propylene glycol monopropyl ether, propylene glycol monobutyl ether, diethylene glycol monoethyl ether, diethylene glycol monobutyl ether, dipropylene glycol n-butyl ether, and mixtures thereof; and
- c) water;

wherein the pH of the composition is from about 2 to about 6;

all weights being relative to the total weight of the composition; and (2) applying onto the hair, a hair color altering composition.

22. A method for controlling the variation in the artificial color of hair, the method comprising:
(1) applying onto the mid-shaft down to the ends of the hair, an acidic pretreatment composition, comprising:
- a) from about 2.5% to about 10% by weight, based on a dry weight basis, of acrylates copolymer, acrylates/hydroxyesters acrylates copolymer and mixtures thereof;
- b) from about 0.01% to about 5% by weight of at least one neutralizing agent selected from monoethanolamine, 2-amino-2-methyl-1-propanol, 2-amino-2-methyl-1,3-propanediol, 3-amino-1,2-propanediol, 3-dimethylamino-1,2-propanediol, and mixtures thereof;
- c) from about 1% to about 20% by weight of at least one organic solvent; and
- d) water;

wherein the pH of the composition is from about 2 to about 6 all weights being relative to the total weight of the composition; and (2) applying onto the roots up to the ends of the hair, a hair color altering composition.

23. A kit comprising:
(1) an individually packaged hair pretreatment composition comprising:
- a) from about 2.5% to about 10% by weight, based on a dry weight basis, of at least one film-forming latex polymer;
- b) at least one neutralizing agent;
- c) from about 1% to about 20% by weight, of at last one organic solvent; and
- d) water;

wherein the pH of the composition is from about 2 to about 6;

all weights being relative to the total weight of the composition;

(2) an individually packaged composition comprising a color-altering agent selected from oxidative dye precursors, direct dyes, pigments, lightening agents, bleaching agents, oxidizing agents, and mixtures thereof; and (3) optionally, an individually packaged composition comprising at least one oxidizing agent.

24. A system for controlling the coloration of hair, the system comprising:
(1) an acidic hair pretreatment composition comprising:
- a) from about 2.5% to about 10% by weight, based on a dry weight basis, of at least one film-forming latex polymer;
- b) at least one neutralizing agent;
- c) from about 1% to about 20% by weight, of at last one organic solvent; and
- d) water;

wherein the pH of the composition is from about 2 to about 6;

all weights being relative to the total weight of the composition;

(2) a composition comprising a color-altering agent selected from oxidative dye precursors, direct dyes, pigments, lightening agents, bleaching agents, oxidizing agents, and mixtures thereof; and (3) optionally, a composition comprising at least one oxidizing agent.

25. A method of making an acidic pretreatment composition for application to the hair comprising:
(1) combining
- a) from about 2.5% to about 10% by weight, based on a dry weight basis, of at least one film-forming latex polymer;
- b) at least one neutralizing agent;
- c) from about 1% to about 20% by weight, of at least one organic solvent; and
- d) water;

wherein the pH of the composition is from about 2 to about 6; all weights being relative to the total weight of the composition; and (2) mixing components (a) to (d) until uniformly distributed.

* * * * *